US012223086B2

(12) United States Patent
Rasanen et al.

(10) Patent No.: US 12,223,086 B2
(45) Date of Patent: Feb. 11, 2025

(54) IMMUTABLE-LEDGER-BASED WORKFLOW MANAGEMENT FOR PATIENT SAMPLES

(71) Applicant: Leica Biosystems Melbourne PTY LTD, Mount Waverley (AU)

(72) Inventors: Misa-Mikko Rasanen, Mt. Waverly (AU); Orlando Skeete, Prahran (AU); Zbigniew Mioduszewski, Ringwood North (AU)

(73) Assignee: Leica Biosystems Melbourne PTY LTD, Mount Waverley (AU)

( * ) Notice: Subject to any disclaimer, the term of this patent is extended or adjusted under 35 U.S.C. 154(b) by 258 days.

(21) Appl. No.: 17/756,032

(22) PCT Filed: Nov. 25, 2020

(86) PCT No.: PCT/IB2020/061154
§ 371 (c)(1),
(2) Date: May 13, 2022

(87) PCT Pub. No.: WO2021/105904
PCT Pub. Date: Jun. 3, 2021

(65) Prior Publication Data
US 2022/0405422 A1 Dec. 22, 2022

Related U.S. Application Data

(60) Provisional application No. 62/940,366, filed on Nov. 26, 2019.

(51) Int. Cl.
*G06F 21/62* (2013.01)
*G16H 10/40* (2018.01)
(Continued)

(52) U.S. Cl.
CPC ........ *G06F 21/6245* (2013.01); *G16H 10/40* (2018.01); *G16H 10/60* (2018.01); *H04L 9/50* (2022.05)

(58) Field of Classification Search
None
See application file for complete search history.

(56) References Cited

U.S. PATENT DOCUMENTS 8,214,899 B2 * 7/2012 Chien ................ G06F 21/552
726/23
11,068,978 B1 * 7/2021 Ferreira ............. H04L 9/3239
(Continued)

FOREIGN PATENT DOCUMENTS

WO    WO 2017/087769 A1    5/2017

OTHER PUBLICATIONS

International Search Report and Written Opinion dated Feb. 2, 2021, for International Application No. PCT/IB2020/061154, 9 pages.

*Primary Examiner* — Boris D Grijalva Lobos
(74) *Attorney, Agent, or Firm* — FROST BROWN TODD LLP (57) ABSTRACT

Blockchain-based workflow management for patient samples. In an embodiment, for each of a plurality of first devices, a request for a unique sample identifier is received from the first device, and, in response to the request, the unique sample identifier is generated and sent to the first device. Then, for each of a plurality of second devices and for each of a plurality of interactions, interaction information is received from the second device, a transaction is generated from the interaction information, and the transaction is recorded in an immutable ledger. The interaction information may comprise a unique sample identifier, a user identifier, a location, an event type, and a timestamp.

16 Claims, 4 Drawing Sheets

(51) Int. Cl.
*G16H 10/60* (2018.01)
*H04L 9/00* (2022.01)

(56) References Cited

U.S. PATENT DOCUMENTS

| | | | |
|---|---|---|---|
| 2015/0332283 A1 | 11/2015 | Witchey | |
| 2017/0272336 A1* | 9/2017 | Johnstone | H04L 43/0817 |
| 2018/0082043 A1 | 3/2018 | Witchey et al. | |
| 2018/0227119 A1* | 8/2018 | Bibera | G06F 16/21 |
| 2019/0180850 A1* | 6/2019 | Shvartsman | G16H 10/40 |
| 2020/0090795 A1* | 3/2020 | Chang | G06F 21/552 |
| 2020/0134202 A1* | 4/2020 | Sapuntzakis | G06F 21/602 |
| 2020/0327250 A1* | 10/2020 | Wang | G06N 20/00 |
| 2020/0366473 A1* | 11/2020 | Brooks | H04L 9/30 |
| 2020/0380475 A1* | 12/2020 | Krueger | G06Q 20/065 |
| 2021/0097385 A1* | 4/2021 | Gupta | G06F 17/40 |

\* cited by examiner

IMMUTABLE-LEDGER-BASED WORKFLOW MANAGEMENT FOR PATIENT SAMPLES

BACKGROUND

Field of the Invention

The embodiments described herein are generally directed to workflow management, and, more particularly, to immutable-ledger-based workflow management for samples, such as tissue specimens from patients.

Description of the Related Art

Immutable ledgers are a promising tool in the context of asset management. Specifically, the use of a modification-resistant ledger (i.e., implemented as a blockchain or directed acyclic graph (DAG)) practically ensures accurate and immutable tracking of assets. Such tracking would be especially useful in the tracking of samples, such as those collected on microscope slides for digital pathology and other medical uses, from collection to archival.

However, the medical context presents unique privacy concerns for specimen tracking. Specifically, individually identifiable health information is governed, for example, by the Health Insurance Portability and Accountability Act (HIPAA). For this reason, a public ledger of health information related to patients' specimens should not be provided.

SUMMARY

Accordingly, systems, methods, and non-transitory computer-readable media are disclosed for immutable-ledger-based workflow management for patient samples (e.g., tissue specimens).

In an embodiment, a method is disclosed that comprises using at least one hardware processor of a user device to: for each of a plurality of first devices, receive a request for a unique sample identifier from the first device over at least one network, and, in response to the request, generate the unique sample identifier, and send the generated unique sample identifier to the first device over the at least one network; and, for each of a plurality of second devices, for each of a plurality of interactions, receive interaction information for the interaction from the second device over the at least one network, wherein the interaction information comprises a unique sample identifier, a user identifier, a location, an event type, and a timestamp, generate a transaction from the interaction information, and record the transaction in an immutable ledger. The immutable ledger may be a blockchain or a directed acyclic graph.

In an embodiment, the method further comprises using at least one hardware processor to analyze transactions in the immutable ledger to calculate one or more metrics for interactions represented by the transactions. The one or more metrics may comprise a throughput rate for one or more of a particular user identifier, location, or event type.

In an embodiment, the method further comprises using at least one hardware processor to retrieve a history comprising all transactions in the immutable ledger that are associated with a particular unique sample identifier. This method may further comprise using at least one hardware processor to display a representation of the history, along with a digital image of a sample identified by the particular unique sample identifier, within a graphical user interface.

In an embodiment, the method further comprises using the at least one hardware processor of the server system to: receive a request to access the immutable ledger from a user over the at least one network; and, in response to the request, provide read-only access to the user to only a subset of transactions in the immutable ledger, while preventing access by the user to any other transactions in the immutable ledger.

These methods may be embodied in executable software modules of a processor-based system, such as a server, and/or in executable instructions stored in a non-transitory computer-readable medium.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

In an embodiment, systems, methods, and non-transitory computer-readable media are disclosed for immutable-ledger-based workflow management for patient samples (e.g., tissue specimens). As used herein, the term "immutable ledger" refers to a virtual ledger in which past transactions (i.e., transactions that have been added to the ledger) cannot feasibly be modified due to practical limits on computing resources. Accordingly, the term "immutable ledger" may refer to a virtual ledger in which past transactions are theoretically modifiable, as long as such modification is not practically possible.

After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. System Overview

1.1. Infrastructure

Figure 1A:
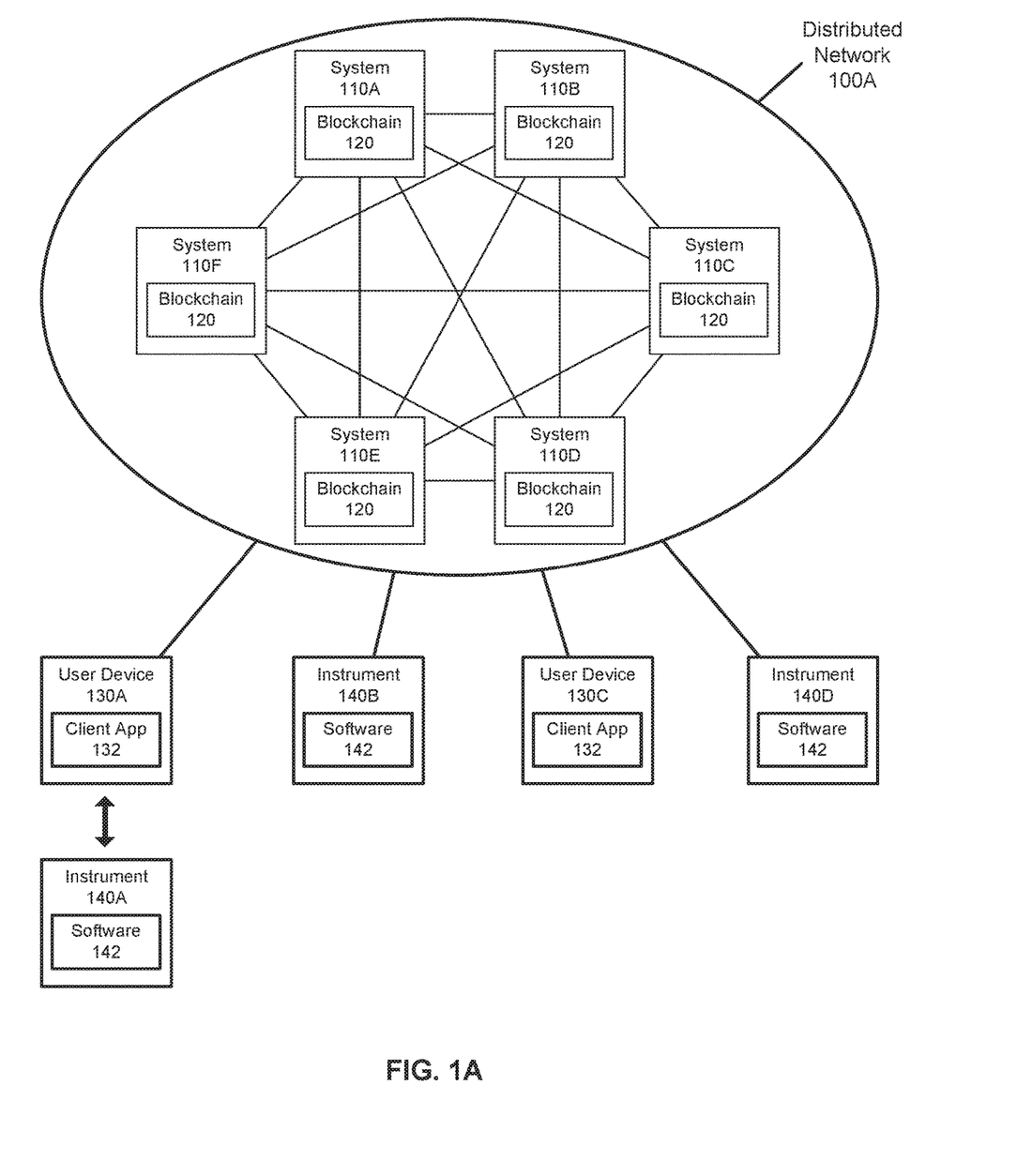
FIGS. 1A and 1B are block diagrams that illustrate example infrastructures, in which one or more of the processes described herein, may be implemented, according to embodiments.

FIG. 1A illustrates an example system for blockchain-based workflow management for patient samples (e.g., tissue specimens), according to an embodiment. The backbone of the workflow management is blockchain network 100. Blockchain network 100 may comprise a plurality of systems 110 connected as nodes in a peer-to-peer network. Systems 110 may be connected via any wired or wireless, public or private, network or networks, including the Internet, and may communicate via any standard or proprietary communication protocols. Systems 110 may comprise the networked computers (e.g., personal computers, servers, etc.) of the entity or entities involved in collecting and processing samples, the entity or entities that manufacture the devices used to collect and process samples, and/or third parties. In an embodiment, blockchain network 100 may be implemented using open-source technology, such as Hyperledger Fabric™ by IBM™.

Each node (i.e., system 110) within blockchain network 100 comprises a complete copy of blockchain 120. Blockchain 120 represents a ledger of all transactions involving the samples whose workflows are being managed by blockchain network 100. As is well-known in the art, blockchain 120 is an open, distributed ledger that is resistant to modification. Specifically, blockchain 120 comprises a plurality of chronologically arranged blocks that are chained together using cryptography. As transactions are created, batches of valid transactions are packaged into a new block along with a cryptographic hash of the most recent block added to blockchain 120. A cryptographic hash of the new block is then generated and the new block with its cryptographic hash is added to blockchain 120. In theory, blockchain 120 could be altered. However, since the blocks are chained together via their cryptographic hashes, in order to alter blockchain 120, the entire blockchain 120 would need to be recomputed, thereby rendering such an undertaking computationally impractical.

Within blockchain network 100, each node (i.e., system 110) is capable of validating transactions, generating new blocks, and broadcasting generated blocks to the other nodes. Since multiple nodes may generate and broadcast new blocks, a consensus method is used to select the next block to be added to blockchain 120. For example, in a blockchain that uses a proof-of-work method, temporary forks may result with different nodes having different versions of blockchain 120, but eventually the chain with the most cumulative proof-of-work will win out. In an embodiment, blockchain network 100 utilizes a proof-of-stake method, in which a node is selected to produce the next valid block in blockchain 120, based on the node's stake (e.g., wealth and/or age) in blockchain 120. Proof-of-stake methods prevent malicious actors by ensuring that they have a stake in the integrity of blockchain 120.

In an embodiment, the physical computational resources required for blockchain 120 are provided as a standard client service (e.g., executing on each of a plurality of user devices 130) that operates as part of blockchain network 100. In this case, access to blockchain network 100 may be contingent upon users continuing to provide mining capacity (e.g., on their user devices 130).

Generally, blockchain 120 is open and viewable by anyone with access to a system 110 storing a copy of blockchain 120. However, the parties to each transaction may be anonymous. In an embodiment, software may be provided (e.g., in a client application 132) that allows a particular user to view, search, and otherwise organize or manage all transactions pertaining to that user on blockchain 120 (e.g., all transactions involving that user's electronic address or other identifier, or within that user's responsibility or purview), in a convenient, permissions-based graphical user interface.

In an embodiment, blockchain 120 utilizes a cryptocurrency, similar to Bitcoin, that may be transferred between the electronic wallets of parties. The cryptocurrency may be used for value transactions associated with testing samples. For example, one laboratory may use the cryptocurrency to pay another laboratory as part of a transaction (e.g., outsourced testing), an insurer may use the cryptocurrency to pay a hospital bill, and a social health care system (e.g., Medicare/Medicaid) may use the cryptocurrency to reimburse patients for medical bills. In addition, an insurer could review each transaction suite (e.g., including transactions for surgery, primary laboratory testing, outsourced laboratory testing, and/or other paid services within the chain of events leading to diagnosis) recorded in the ledger of blockchain 120, and use the cryptocurrency to pay each transaction suite. In an embodiment, the cryptocurrency may also be mined, in order to provide parties an incentive to lend their computational resources to blockchain network 100.

Figure 1B:
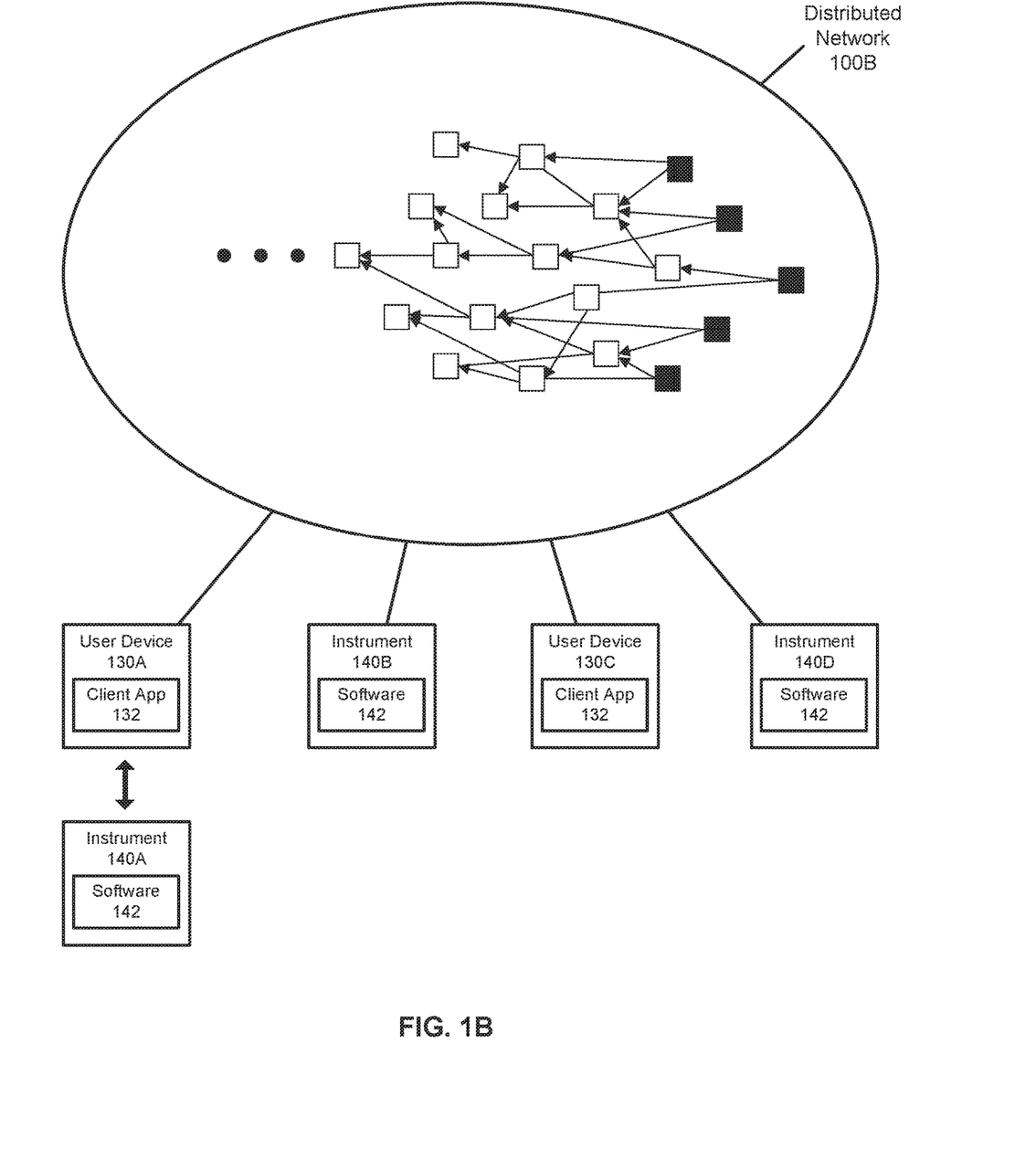

In an alternative embodiment, another implementation or type of immutable ledger may be used to record each of the described transactions. FIG. 1B illustrates an example system for immutable-ledger-based workflow management for patient samples (e.g., tissue specimens) that utilizes a directed acyclic graph (DAG), according to an embodiment. For example, instead of blockchain 120, an alternative embodiment may use a DAG, such as Tangle™. A DAG is a hierarchy of nodes without any cycles. DAGs can be beneficial if the number of users is expected to be large. In contrast to blockchains, DAGs get faster as the number of users increase and do not require miners. However, DAGs are more vulnerable than blockchains when the network size is small. In a DAG, in order for a user to add a transaction, that user must approve two unconfirmed transactions that have been randomly chosen (e.g., using a Markov Chain Monte Carlo (MCMC) algorithm, which ensures that a user does not choose the user's own transaction). Like a blockchain, DAGs may utilize a cryptocurrency (e.g., IOTA in Tangle™).

Regardless of the particular immutable ledger that is used, the transactions in the immutable ledger may comprise collection of the samples (e.g., via surgery), processing of the samples (e.g., to prepare and mount specimens on glass slides), archiving of the samples (e.g., in physical or digital storage), and/or the like. Each transaction may identify the sample(s) involved in the transaction, one or more parties involved in the transaction, a location (e.g., location of the scan, data entry, or other event which produced the transaction), a transaction or event type (e.g., the type of interaction involved in the transaction), and a time (e.g., a timestamp representing the day and time of the scan, data entry, or other event which produced the transaction). Each transaction may also comprise any additional information that is relevant to the transaction, such as an identifier of the operator who performed the interaction represented by the transaction, the current temperature during the interaction represented by the transaction, lot numbers of reagents or other consumables used during the interaction represented by the transaction, and/or the like.

User device(s) 130 communicate with distributed network 100 via wired or wireless, public or private, network or networks, including the Internet. User device(s) 130 may comprise any type or types of computing devices capable of wired and/or wireless communication, including without limitation, desktop computers, laptop computers, tablet computers, smart phones or other mobile phones, servers, game consoles, televisions, set-top boxes, electronic kiosks, point-of-sale terminals, and/or the like. However, in a preferred embodiment, user device(s) 130 comprise a wireless device (e.g., smartphone or tablet) that communicates over a wireless network (e.g., cellular and/or Wi-Fi™ network) and comprises a camera or other device (e.g., laser scanner, for example, housed in a wand) capable of reading machine-readable indicia (e.g., barcodes, Quick Response (QR)

codes, radio-frequency identification (RFID) tags, etc.). Each user device 130 may store and execute a client application 132, which implements one or more of the functions described herein.

Instrument(s) 140 process the samples described herein. For example, instrument(s) 140 may comprise the tissue processing systems and/or staining systems provided by Leica Biosystems™. As an example, instrument 140 may comprise the BOND-III Fully Automated IHC and ISH Stainer, Aperio GT 450, and/or the like, from Leica Biosystems™. For privacy or other reasons, some instruments, such as instrument 140A, may be offline, such that they are not able to communicate with distributed network 100. Other instruments, such as instruments 140B and 140D, may be online, such that they are able to communicate with distributed network 100 via wired or wireless, public or private, network or networks, including the Internet. In either case, each instrument 140 may store and execute software 142, which implements one or more of the functions described herein, including separate processes depending on whether the instrument 140 is online or offline.

1.2. Example Processing Device

Figure 2:
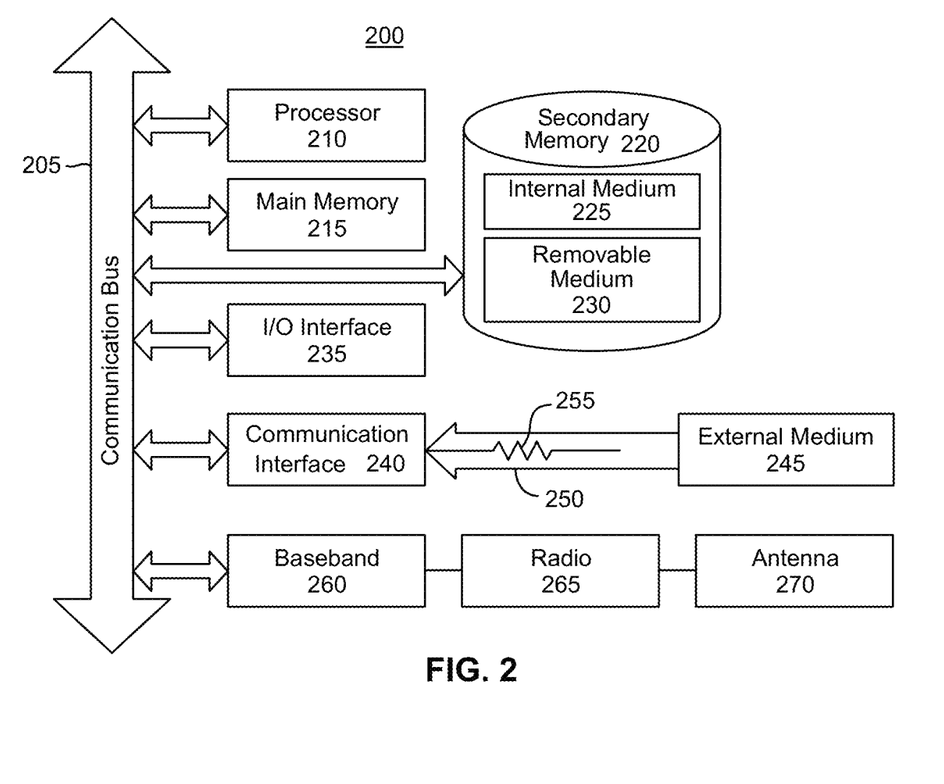
FIG. 2 is a block diagram that illustrates an example processing system, by which one or more of the processed described herein, may be executed, according to an embodiment.

FIG. 2 is a block diagram illustrating an example wired or wireless system 200 that may be used in connection with various embodiments described herein. For example, system 200 may be used as or in conjunction with one or more of the functions, processes, or methods (e.g., to store and/or execute client application 132 and/or software 142, or one or more modules of client application 132 and/or software 142) described herein, and may represent components of distributed network 100, system(s) 110, user device(s) 130, instrument(s) 140, and/or other processing devices described herein. System 200 can be a server or any conventional personal computer, or any other processor-enabled device that is capable of wired or wireless data communication. Other computer systems and/or architectures may be also used, as will be clear to those skilled in the art.

System 200 preferably includes one or more processors, such as processor 210. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 210. Examples of processors which may be used with system 200 include, without limitation, the Pentium® processor, Core i7® processor, and Xeon® processor, all of which are available from Intel Corporation of Santa Clara, California.

Processor 210 is preferably connected to a communication bus 205. Communication bus 205 may include a data channel for facilitating information transfer between storage and other peripheral components of system 200. Furthermore, communication bus 205 may provide a set of signals used for communication with processor 210, including a data bus, address bus, and/or control bus (not shown). Communication bus 205 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 200 preferably includes a main memory 215 and may also include a secondary memory 220. Main memory 215 provides storage of instructions and data for programs executing on processor 210, such as one or more of the functions and/or modules discussed herein. It should be understood that programs stored in the memory and executed by processor 210 may be written and/or compiled according to any suitable language, including without limitation C/C++, Java, JavaScript, Perl, Visual Basic, .NET, and the like. Main memory 215 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 220 may optionally include an internal medium 225 and/or a removable medium 230. Removable medium 230 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 220 is a non-transitory computer-readable medium having computer-executable code (e.g., disclosed software modules) and/or other data stored thereon. The computer software or data stored on secondary memory 220 is read into main memory 215 for execution by processor 210.

In alternative embodiments, secondary memory 220 may include other similar means for allowing computer programs or other data or instructions to be loaded into system 200. Such means may include, for example, a communication interface 240, which allows software and data to be transferred from external storage medium 245 to system 200. Examples of external storage medium 245 may include an external hard disk drive, an external optical drive, an external magneto-optical drive, and/or the like. Other examples of secondary memory 220 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 200 may include a communication interface 240. Communication interface 240 allows software and data to be transferred between system 200 and external devices (e.g. printers), networks, or other information sources. For example, computer software or executable code may be transferred to system 200 from a network server (e.g., platform 110) via communication interface 240. Examples of communication interface 240 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 200 with a network (e.g., network(s) 120) or another computing device. Communication interface 240 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 240 are generally in the form of electrical communication signals 255. These signals 255 may be provided to communication interface 240 via a communication channel 250. In an embodiment, communication channel 250 may be a wired or wireless network (e.g., network(s) 120), or any variety of other communication links. Communication channel 250 carries signals 255 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 215 and/or secondary memory 220. Computer programs can also be received via communication interface 240 and stored in main memory 215 and/or secondary memory 220. Such computer programs, when executed, enable system 200 to perform the various functions of the disclosed embodiments as described elsewhere herein.

In this description, the term "computer-readable medium" is used to refer to any non-transitory computer-readable storage media used to provide computer-executable code and/or other data to or within system 200. Examples of such media include main memory 215, secondary memory 220 (including internal memory 225, removable medium 230, and external storage medium 245), and any peripheral device communicatively coupled with communication interface 240 (including a network information server or other network device). These non-transitory computer-readable media are means for providing executable code, programming instructions, software, and/or other data to system 200.

In an embodiment that is implemented using software, the software may be stored on a computer-readable medium and loaded into system 200 by way of removable medium 230, I/O interface 235, or communication interface 240. In such an embodiment, the software is loaded into system 200 in the form of electrical communication signals 255. The software, when executed by processor 210, preferably causes processor 210 to perform one or more of the processes and functions described elsewhere herein.

In an embodiment, I/O interface 235 provides an interface between one or more components of system 200 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 200 may also include optional wireless communication components that facilitate wireless communication over a voice network and/or a data network (e.g., in the case of user system 130). The wireless communication components comprise an antenna system 270, a radio system 265, and a baseband system 260. In system 200, radio frequency (RF) signals are transmitted and received over the air by antenna system 270 under the management of radio system 265.

In an embodiment, antenna system 270 may comprise one or more antennae and one or more multiplexors (not shown) that perform a switching function to provide antenna system 270 with transmit and receive signal paths. In the receive path, received RF signals can be coupled from a multiplexor to a low noise amplifier (not shown) that amplifies the received RF signal and sends the amplified signal to radio system 265.

In an alternative embodiment, radio system 265 may comprise one or more radios that are configured to communicate over various frequencies. In an embodiment, radio system 265 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 265 to baseband system 260.

If the received signal contains audio information, then baseband system 260 decodes the signal and converts it to an analog signal. Then the signal is amplified and sent to a speaker. Baseband system 260 also receives analog audio signals from a microphone. These analog audio signals are converted to digital signals and encoded by baseband system 260. Baseband system 260 also encodes the digital signals for transmission and generates a baseband transmit audio signal that is routed to the modulator portion of radio system 265. The modulator mixes the baseband transmit audio signal with an RF carrier signal, generating an RF transmit signal that is routed to antenna system 270 and may pass through a power amplifier (not shown). The power amplifier amplifies the RF transmit signal and routes it to antenna system 270, where the signal is switched to the antenna port for transmission.

Baseband system 260 is also communicatively coupled with processor 210, which may be a central processing unit (CPU). Processor 210 has access to data storage areas 215 and 220. Processor 210 is preferably configured to execute instructions (i.e., computer programs, such as the disclosed application, or software modules) that can be stored in main memory 215 or secondary memory 220. Computer programs can also be received from baseband processor 260 and stored in main memory 210 or in secondary memory 220, or executed upon receipt. Such computer programs, when executed, enable system 200 to perform the various functions of the disclosed embodiments.

2. Process Overview

Embodiments of processes for immutable-ledger-based workflow management for patient samples (e.g., tissue specimens) will now be described in detail. It should be understood that the described processes may be embodied in one or more software modules that are executed by one or more hardware processors (e.g., processor 210), for example, as the software applications discussed herein (e.g., client application 132 and/or software 142). The described process may be implemented as instructions represented in source code, object code, and/or machine code. These instructions may be executed directly by the hardware processor(s), or alternatively, may be executed by a virtual machine operating between the object code and the hardware processors. In addition, the disclosed application may be built upon or interfaced with one or more existing systems.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

Furthermore, while the processes, described herein, are illustrated with a certain arrangement and ordering of steps, each process may be implemented with fewer, more, or different steps and a different arrangement and/or ordering of steps. In addition, it should be understood that any step, which does not depend on the completion of another step, may be executed before, after, or in parallel with that other independent step, even if the steps are described or illustrated in a particular order.

2.1. Workflow Tracking

Figure 3:
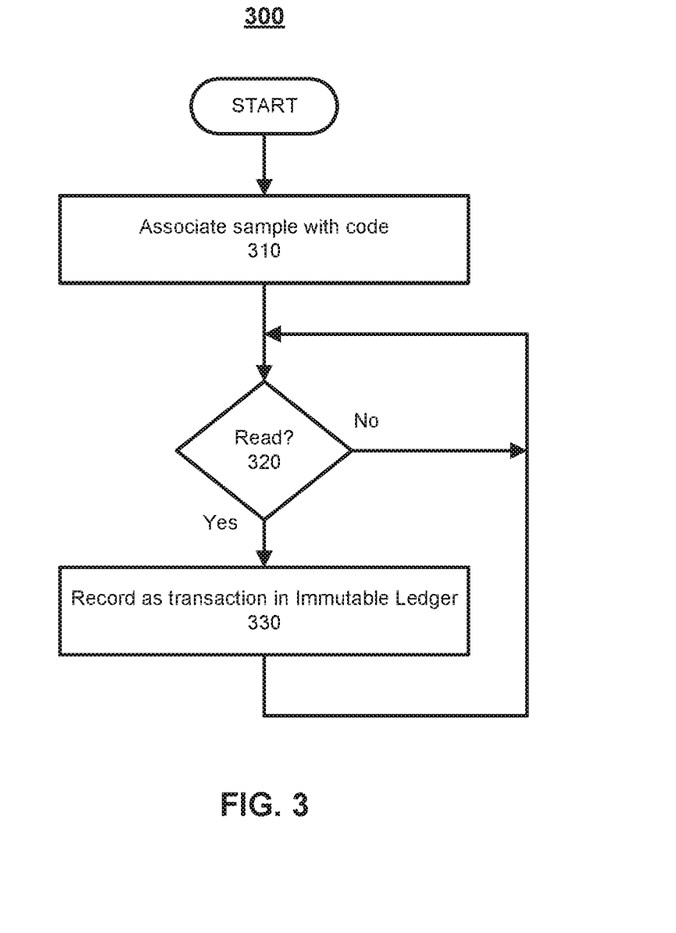
FIG. 3 is a flowchart that illustrates a process for immutable-ledger-based workflow management, according to an embodiment.

FIG. 3 is a flowchart that illustrates a process 300 for immutable-ledger-based workflow tracking, according to an embodiment. In an embodiment, the immutable ledger represents all "touch points" for each sample from collection to analysis to archival. Each touch point may be represented in the immutable ledger as a transaction comprising a timestamp representing the time at which the touch point occurred, an identifier of the handler (e.g., surgeon, technician, archivist, etc.) at the touch point, an identifier of the sample handled at the touch point, a location of the touch point, a temperature of the sample at the touch point, and/or the like. Each transaction could comprise additional information as well, such as results from one or more tests (e.g., readouts from analyzers performed on the sample, including manually dictated or recorded reports from pathologists or other medical professionals, documents or formal reports, etc.). The set of touch points for a given sample (e.g., spanning collection to archival) may be referred to as a "transaction suite." The tracking of touch points allows metrics for each sample to be tracked, such as the time between extraction of the sample and placement of the sample in formalin (e.g., by calculating the difference between the timestamp of a transaction recording the extraction of a particular sample and a timestamp of a transaction recording the placement in formalin of that particular sample).

In an embodiment, the workflow that is tracked for each sample may comprise collection of the sample, preparation of the sample, mounting of the sample (e.g., on a glass slide), imaging of the sample (e.g., via an automated slide scanning system), testing of the sample, archiving of the sample, and/or the like. The archival process may comprise physical archiving of the sample (e.g., within a facility) and/or archiving of a digital image of the sample.

In step 310, a sample is associated with an identifier that uniquely identifies the sample from all other samples. The sample identifier may also encode relationships between samples (e.g., by comprising an identical segment, within a prefix or suffix, as one or more other sample identifiers), such as divided samples which are too large to process whole or multiple samples from an individual patient that collectively comprise one case. Each sample identifier may be encoded into a machine-readable indicium, such as a barcode or QR code, that can be applied to the sample holder. For example, the machine-readable indicium may be printed on a label that is applied to the glass microscope slide holding the sample. Thus, the machine-readable indicium may be read via a reading device, which, in the context of a barcode or QR code, may comprise a barcode reader or camera. Alternatively, the machine-readable indicium may be a radio-frequency identification (RFID) tag or other wireless transmitter that transmits a signal, encoding the unique identifier, which can be read wirelessly by an antenna-based reading device (e.g., RFID interrogator).

The unique identifier for a given sample may be obtained contemporaneously with acquisition of the sample. For example, before, as, or after the sample is collected, a user (e.g., surgeon, nurse, or other individual collecting the sample) may interact with a user device 130 that communicates with distributed network 100 to obtain a new unique identifier. The issuance of a new unique identifier may be automatically recorded as a transaction in the immutable ledger upon issuance. Once obtained, user device 130 may provide the unique identifier to the user (e.g., via a graphical user interface of client app 132) and/or encode the unique identifier into a machine-readable indicium to be applied to the sample (e.g., by initiating printing of a label with the machine-readable indicium). Additionally, when required by laboratory regulations, human-readable versions of the unique identifier may be combined with the machine-readable indicium and applied to the sample together with the machine-readable indicium to form an indicium that is both machine-readable and human-readable. The user may then apply the indicium to the sample holder (e.g., by adhering a printed label with the indicium to a label portion of the glass slide on which the sample is held).

In step 320, process 300 waits for a unique sample identifier to be read at a touch point. A touch point may comprise any interaction with the sample, including, for example, collection of the sample, any processing of the sample (e.g., digital imaging, laboratory testing, etc.), archival of the sample, and/or the like. A read may comprise a manual scan (e.g., using a camera, laser scanning wand, etc., of a user device 130), a manual entry (e.g., using an input device of a user device 130), and/or an automatic scan (e.g., by an online instrument 140) of the machine-readable indicium encoding the unique sample identifier. For online instruments (e.g., instruments 140B and 140D in FIG. 1), the instrument 140 may scan the machine-readable indicium. This scan may be performed manually using a wand or other scanning device attached or integral to instrument 140, or automatically by instrument 140 after the sample has been loaded into instrument 140. If the unique sample identifier is read at a touch point (i.e., "Yes" in step 320), process 300 proceeds to step 330. Otherwise (i.e., "No" in step 320), process 300 continues to wait for a unique sample identifier to be read at a touch point.

In step 330, each read is communicated to distributed network 100 as a transaction (e.g., to be incorporated into a new block on blockchain 120 or into a new node of the DAG). This communication may be done in real time or near-real time with respect to the time that the read occurs. Specifically, the unique sample identifier of the sample may be packaged with additional information into a message that is transmitted to distributed network 100 (e.g., to a system 110) that packages the information from the message into a transaction that is incorporated into the immutable ledger. In an embodiment, this additional information comprises a user identifier (e.g., identifying the user or user device 130 associated with the touch point), a location (e.g., identifying the location of the touch point, for example, using a facility and/or terminal identifier), an event type (e.g., indicating the type of interaction with the sample at the touch point), and a timestamp (e.g., indicating the time of the interaction with the sample at the touch point). Alternatively or additionally, the additional information may comprise other information (e.g., details of the interaction with the sample, such as the tests or other processing being performed, temperature or other environmental metric at the touch point, etc.).

The additional information may be acquired automatically and/or manually. At least some of the information may be manually input by a user via a graphical user interface of client application 132 on user device 130, while other information may be automatically acquired or inferred. Alternatively, all of the information may be automatically acquired, or all of the information may be manually acquired. As an example, the user identifier may be automatically determined based on the user (e.g., from a user account or profile) who is currently logged into the user system 130 or instrument 140 that performed the read in step 320. Similarly, the location may be automatically determined based on the location of the user system 130 or instrument 140 that performed the read in step 320 (e.g., a location set in the memory of user system 130 or instrument 140, a location acquired from a Global Positioning System (GPS) within user system 130 or instrument 140, etc.), and the timestamp may be automatically generated (e.g., as the current time) by the user system 130 or instrument 140 that performed the read in step 320. The event type could be automatically determined based on the user (e.g., based on a role in the user's account or profile) who is currently logged into the user system 130 or instrument 140 that performed the read in step 320, the type of instrument 140 that was performed the read or was used, the location of the user system 130 or instrument 140 that performed the read in step 320, a manual entry or selection input by the user, a user or system setting, and/or the like.

In an embodiment, to ensure that only authentic transactions are added to the immutable ledger, only authenticated users or devices may produce transactions. Specifically, a user or device (e.g., user system 130 or instrument 140) may be required to authenticate with distributed network 100, prior to creating transactions, using any well-known authentication mechanisms (e.g., digital keys, username and password, etc.). Distributed network 100 may ignore or discard any messages from non-authenticated users or devices.

In an embodiment, before a transaction, involving a sample identifier, is added to the immutable ledger, distributed network 100 may first confirm that the sample identifier and/or transaction are valid. For instance, an invalid sample identifier may be one for which there is no transaction in the immutable ledger that represents issuance of that sample identifier. An invalid transaction may comprise any inappropriate or unexpected transaction. As an example, a transaction with an event type that is something other than collection, but which occurs when there is not a prior collection transaction in the immutable ledger, may be considered invalid (e.g., because it is assumed that a sample cannot be processed or archived before it is collected). When performing validation, a node (i.e., system 110) in distributed network 100 may refer to a copy of the immutable ledger (e.g., its copy of blockchain 120) to ensure that the sample identifier has been issued and the transaction to be recorded is appropriate in view of any previous transactions in the immutable ledger that involve the same sample identifier.

In general, patient information should never be included in any of the machine-readable indicia described herein. More generally, patient information should never be sent to distributed network 100 or recorded in the immutable ledger. This maintains patient privacy and ensures that the disclosed embodiments pose no threat to the security of patient information.

It should be understood that process 300 may be applied to a plurality of different samples in parallel and/or serially. For example, steps 320 and 330 may be performed in parallel, in real time, for a plurality of reads of different sample identifiers. In addition, reads in step 320 may include bulk reads of a plurality of sample identifiers (e.g., a storage or transport device holding a plurality of samples) at once. Thus, a plurality of samples (e.g., hundreds, thousands, millions, billions of samples) may be tracked through many iterations of process 300 to produce a ledger in distributed network 100 that comprises a plurality of transactions for each of the plurality of samples. The ledger provides an immutable record of every touch point on every sample that is being tracked.

2.2. Access Restrictions

In an embodiment, access to the immutable ledger may be restricted based on user roles and/or permissions. Specifically, regular users may have access to only a subset of transactions in the immutable ledger (e.g., only transactions for particular sample(s), user(s), device(s), and/or location(s)). For example, a surgeon may only be able to access transactions (e.g., collection transactions) created by the surgeon and/or the surgeon's department. As another example, a user who needs to verify a particular sample may have access to all transactions involving that particular sample (e.g., to verify that all appropriate tests were performed), but no access to transactions for other samples. However, it should be understood that there may be users (e.g., administrative users) who have access to the entire ledger (i.e., every transaction). Advantageously, each user can access the information that is of relevance to them, with full guarantee of data integrity.

2.3. Encryption of Identifiers

In an embodiment, for added security and privacy, one or more of the identifiers included in the transactions in the immutable ledger may be encrypted (e.g., using a hash function) before being added to the transaction. Such encryption would make it more difficult for outsiders to connect the identifier to a specific user (e.g., facility, institution, device, person, etc.).

3. Example Applications and Advantages

By design, the immutable ledger (e.g., blockchain 120 or a DAG) provides an extremely high level of security, traceability, and anti-fraud protection. For example, since the immutable ledger cannot be feasibly altered, there is no database of records that can be corrupted, tampered with, or otherwise altered. All transactions will be indelibly and indefinitely recorded in the immutable ledger, providing a wealth of data for analysis, data mining, and/or the like.

In addition, instead of the multiple information technology (IT) standards that healthcare providers must navigate in conventional systems, interactions with distributed network 100 require only a single set of IT standards. This overcomes the connectivity complexity and need for middleware that arises with conventional systems (e.g., Cerebro™ and Laboratory Information Systems (LIS)), thereby simplifying management of the system. The use of distributed network 100 allows one universal system to be used for the entire workflow.

3.4. Financial Payments

In an embodiment, the immutable ledger may be used to determine, audit, or reconcile financial payments. For example, the ledger provides immutable evidence that interactions have occurred, such as evidence that ordered tests have been performed. This can be used as proof of healthcare for reimbursement by insurers or government authorities.

3.5. Performance Monitoring

In an embodiment, the immutable ledger may be used to measure the performance of one or more health networks. For example, the transactions in the immutable ledger may be analyzed to calculate metrics, such as the number of interactions (e.g., collections, tests, etc.) performed by each user or device (e.g., user system 130 or instrument 140) per unit time (e.g., using the user identifier and timestamps of transactions), the number of interactions at each location per unit time (e.g., using the location and timestamps of transactions), the average time between interactions for each user, device, or location (e.g., using sample identifier, user identifier or location, event type, and timestamps of transactions) and/or the like. Such metrics allow operators to evaluate the performance of their health network, optimize workflow (e.g., increase throughput for sample handling, processing, storage, etc.), troubleshoot (e.g., identify bottlenecks, underutilized resources, over-utilized resources, etc.), and/or the like.

3.6. Tracking Healthcare-Related Events

In an embodiment, the immutable ledger may be used to track healthcare-related events, including adverse events, associated with samples. For example, transactions in the immutable ledger for a particular sample may be analyzed to identify all adverse events associated with that sample or the overall adverse event rate of a particular facility, for benchmarking or to determine penalties.

3.7. Auditing

In an embodiment, the immutable ledger may be used for auditing. For example, a user that needs to verify a particular sample may access the immutable ledger to verify all of the interactions with that particular sample. The user can review the full history of that sample without needing to contact any outside parties or access any other systems. In addition, at least some users may have read-only access to a data repository of digital images of the samples. Such users may be able to view the digital image of a particular sample, along with the entire interaction history (e.g., extracted from the transactions in the immutable ledger) for the sample.

3.8. Sample-Specific Information

In an embodiment, additional information may be associated with sample identifiers over time. Naturally, the machine-readable indicia applied to samples cannot incorporate new information without being reprinted and reapplied to the samples. However, additional information may be associated with the sample identifiers, that are encoded into the machine-readable indicia, such that the additional information can be retrieved based on the machine-readable indicia. In this manner, the information associated with a machine-readable indicium applied to a sample may expand or otherwise change over time without having to change and reapply the machine-readable indicium to the sample.

3.9. Instrument History

In an embodiment, since all sample processing by a particular instrument 140 may be recorded in the immutable ledger, instruments 140 can also be tracked using the immutable ledger. For example, the usage history of each instrument 140 can be inferred from the usage transactions associated with that instrument 140 (e.g., transactions comprising an identifier of the instrument 140). This usage history can be used to produce service and/or repair information (e.g., scheduling a service or repair). For example, assume that the manufacturer recommends that instruments 140 be serviced (e.g., routine checkup, replacement of a particular part, etc.) every one-thousand uses. A software service of the manufacturer and/or customer may continually check the immutable ledger and compute the amount of uses, recorded in transactions in the immutable ledger, for each instrument 140. When the amount of uses for a particular instrument 140 reaches one thousand, the software service can notify a user of the manufacturer and/or customer, automatically schedule a service of instrument 140, prevent instrument 140 from being used until it has been serviced, and/or the like.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

The invention claimed is:

1. A system comprising:
a hardware memory circuit configured to store executable instructions; and
at least one hardware processor configured to:
receive a request for a unique sample identifier for a first sample from a first device over at least one network, the first sample associated with patient information,
in response to the request, generate and send the generated unique sample identifier to the first device over the at least one network, and
for each of a plurality of interactions associated with the first sample:
receive interaction information for the interaction from one of a plurality of second devices over the at least one network, wherein the interaction information comprises the unique sample identifier, a user identifier, a location, an event type, and a timestamp,
generate a transaction from the interaction information, and
record the transaction in an immutable ledger,
wherein the unique sample identifier and all transactions on the immutable ledger are free of patient information;
wherein the at least one hardware processor is further configured to retrieve a history comprising all transactions in the immutable ledger that are associated with a particular unique sample identifier; and
wherein the at least one hardware processor is further configured to display a representation of the history, along with a digital image of a sample identified by the particular unique sample identifier, within a graphical user interface.

2. The system of claim 1, wherein the immutable ledger is a blockchain.

3. The system of claim 1, wherein the immutable ledger is a directed acyclic graph.

4. The system of claim 1, wherein the at least one hardware processor is further configured to analyze transactions in the immutable ledger to determine one or more metrics for interactions represented by the transactions.

5. The system of claim 4, wherein the one or more metrics comprise a throughput rate for one or more of a particular user identifier, location, or event type.

6. The system of claim 1, wherein the at least one hardware processor is further configured to:
receive a request to access the immutable ledger from a user over the at least one network; and,
in response to the request, provide read-only access to the user to only a subset of transactions in the immutable ledger, while preventing access by the user to any other transactions in the immutable ledger.

7. A method performed by at least one hardware processor of a server system, the method comprising:
receiving a request for a unique sample identifier for a first sample from a first device over at least one network, the first sample associated with patient information,
in response to the request, generating and sending the generated unique sample identifier to the first device over the at least one network, and for each of a plurality of interactions associated with the first sample:
receiving interaction information for the interaction from one of a plurality of second devices over the at least one network, wherein the interaction information comprises the unique sample identifier, a user identifier, a location, an event type, and a timestamp, and
generating a transaction from the interaction information, and record the transaction in an immutable ledger,
wherein the unique sample identifier and all transactions on the immutable ledger are free of patient information.

8. The method of claim 7, wherein the immutable ledger is a blockchain.

9. The method of claim 7, wherein the immutable ledger is a directed acyclic graph.

10. The method of claim 7, further comprising analyzing transactions in the immutable ledger to determine one or more metrics for interactions represented by the transactions.

11. A non-transitory computer-readable medium having instructions stored therein, wherein the instructions, when executed by a processor, cause the processor to:
receive a request for a unique sample identifier for a first sample from a first device over at least one network, the first sample associated with patient information,
in response to the request, generate and send the generated unique sample identifier to the first device over the at least one network, and
for each of a plurality of interactions associated with the first sample;
receive interaction information for the interaction from one of a plurality of second devices over the at least one network, wherein the interaction information comprises the unique sample identifier, a user identifier, a location, an event type, and a timestamp,
generate a transaction from the interaction information, and record the transaction in an immutable ledger,
wherein the unique sample identifier and all transactions on the immutable ledger are free of patient information;
wherein the instructions are further configured to cause the processor to retrieve a history comprising all transactions in the immutable ledger that are associated with a particular unique sample identifier; and
wherein the instructions are further configured to cause the processor to display a representation of the history, along with a digital image of a sample identified by the particular unique sample identifier, within a graphical user interface.

12. The non-transitory computer-readable medium of claim 11, wherein the immutable ledger is a blockchain.

13. The non-transitory computer-readable medium of claim 11, wherein the immutable ledger is a directed acyclic graph.

14. The non-transitory computer-readable medium of claim 11, wherein the instructions are further configured to cause the processor to:
analyze transactions in the immutable ledger to determine one or more metrics for interactions represented by the transactions.

15. The non-transitory computer-readable medium of claim 14, wherein the one or more metrics comprise a throughput rate for one or more of a particular user identifier, location, or event type.

16. The non-transitory computer-readable medium of claim 11, wherein the instructions are further configured to cause the processor to:
- receive a request to access the immutable ledger from a user over the at least one network; and,
- in response to the request, provide read-only access to the user to only a subset of transactions in the immutable ledger, while preventing access by the user to any other transactions in the immutable ledger.

\* \* \* \* \*